United States Patent [19]

Schulz et al.

[11] 4,158,739

[45] * Jun. 19, 1979

[54] PROCESS FOR CONVERTING CYCLOPENTANE TO GLUTARIC ACID

[75] Inventors: Johann G. D. Schulz; Anatoli Onopchenko, both of Pittsburgh, Pa.

[73] Assignee: Gulf Research & Development Company, Pittsburgh, Pa.

[*] Notice: The portion of the term of this patent subsequent to Jun. 28, 1994, has been disclaimed.

[21] Appl. No.: 887,943

[22] Filed: Mar. 20, 1978

[51] Int. Cl.$^2$ .............................................. C07C 51/18
[52] U.S. Cl. ..................................... 562/543; 562/590
[58] Field of Search ..................... 260/533 C; 562/543

[56] References Cited

U.S. PATENT DOCUMENTS 4,032,569   6/1977   Onopchenko et al. .............. 562/543

FOREIGN PATENT DOCUMENTS 1007987 10/1965 United Kingdom ..................... 562/543

Primary Examiner—Vivian Garner

[57] ABSTRACT

A process for converting cyclopentane to glutaric acid which involves oxidizing cyclopentane with molecular oxygen in the presence of critical amounts of cobaltic ions in an aliphatic monobasic acid while maintaining critical temperature, pressure and contact time in the reaction zone.

9 Claims, No Drawings

PROCESS FOR CONVERTING CYCLOPENTANE TO GLUTARIC ACID

BACKGROUND OF THE INVENTION

1. Field of the Invention

This invention relates to a process for converting cyclopentane to glutaric acid which comprises oxidizing cyclopentane with molecular oxygen in the presence of critical amounts of cobaltic ions in an aliphatic monobasic acid solvent while maintaining critical temperature, pressure and contact time in the reaction zone.

2. Description of the Prior Art

In our U.S. Pat. No. 4,032,569 we have disclosed a process for converting cyclohexane to adipic acid which involves oxidizing cyclohexane with molecular oxygen in the presence of critical amounts of cobaltic ions in an aliphatic monobasic acid while maintaining critical temperature, pressure and contact time in the reaction zone.

SUMMARY OF THE INVENTION

We have found that significantly higher conversions of cyclopentane to a product predominating in glutaric acid can also be obtained in the process defined above if critical amounts of cobalt are present in the reaction zone, the temperature and pressure during reaction are maintained within critical ranges and if the reaction is terminated within a critical time period.

The components required in the reaction zone are cyclopentane, an aliphatic monobasic acid solvent, cobaltic ions and molecular oxygen.

The solvent used herein can be any aliphatic monobasic acid containing only primary and secondary hydrogen atoms in its structure and having from two to eight carbon atoms, preferably having from two to four carbon atoms. Examples of satisfactory monobasic acid solvents for this reaction include acetic, propionic, normal butyric, caprylic, pelargonic, trimethylacetic, normal caproic acid, etc. Of these we prefer to use acetic acid. The molar ratios of solvent to cyclopentane lie between about 1.5:1 to about 10:1 or even higher, but preferably between about 3:1 to about 9:1.

Cobalt must be present in the form of its cobaltic ion. The source from which the cobaltic ion is obtained is immaterial, as long as cobaltic ions are maintained in the reaction mixture during the reaction period. Thus, as a source thereof any cobaltous or cobaltic salt of an organic acid can be employed, such as cobaltous or cobaltic acetate, propionate, naphthenate, etc. Of these we prefer to use the cobalt acetate salts. In order to assist in obtaining the high conversions herein, the amount of cobalt present in the reaction mixture is critical and must be in excess of about 20 millimols of cobalt per mol of cyclopentane, preferably in the range of about 25 to about 100 millimols of cobalt per mol of cyclopentane. Cobalt in an amount up to about 150 millimols per mol of cyclopentane can be used, but amounts in excess thereof produce no significantly improved results.

In the oxidation of cyclopentane with molecular oxygen there is a period of induction before the reaction begins to proceed. This period of induction is believed to occur in order to oxidize the cobaltous ion to the active cobaltic ion and to promote the production of free radicals from the cyclopentane charge. This induction period can vary, for example, from about ½ to as high as three hours, or even more. The induction period can be reduced, however, by the addition of an initiator to the reaction mixture. We believe the function of the initiator is to form free radicals faster than the cyclopentane will form free radicals and to act as an oxidant to convert the cobaltous ion into the active cobaltic ion. The initiators can be, for example, any compounds in which oxygen has a valence of minus one or compounds which on reacting with molecular oxygen will form compounds which contain oxygen having a valence of minus one. Compounds that can be used include, for example, ozone; inorganic peroxides, such as sodium or hydrogen peroxide; organic peroxides, such as benzoyl peroxides; peracids, such as peracetic acid; aldehydes, such as acetaldehyde; ketones, such as methyl ethyl ketone and cyclohexanone; ethers, such as dimethyl ether; halides such as sodium bromide, etc. We prefer to employ cyclic hydroperoxides or cyclic ketones corresponding in carbon structure to the cyclic hydroperoxides and cyclic ketones produced in the reaction. The amount of initiator can vary between about 0.1 to about 20 weight percent based on the cyclopentane with preferred amounts of initiator being between about 0.3 to about three weight percent based on the cyclopentane.

Free molecular oxygen must also be present in the reaction zone. Thus, either air or oxygen itself can be employed. Another critical requirement herein in obtaining high conversions of cyclopentane to glutaric acid is the partial pressure of oxygen over the reaction mixture. We have found that such partial pressure must be at least about 175 pounds per square inch (about 11.9 kilograms per square centimeter) and can be as high as about 600 pounds per square inch (about 40.8 kilograms per square centimeter), or even higher, but excellent conversions are obtained when the oxygen pressure is in the range of about 200 to about 500 pounds per square inch absolute (about 13.6 to about 34.0 kilograms per square centimeter). Such pressures, moreover, are sufficient to maintain the reactants in the liquid phase.

The reaction temperature is also critical and must be maintained in the range of about 70° to about 150° C., preferably in the range of about 80° to about 120° C. We have found that when temperatures in excess of the defined temperature ranges are employed there is an increasing tendency toward degradation of the desired glutaric acid to succinic acid. The reaction tends to go at an exceedingly slow rate below the defined temperature ranges and would therefore be commercially unattractive.

We have also found that reaction time is also critical, in that a short reaction time, from about 0.5 to about three hours, preferably about one to about two hours is sufficient to obtain the desired high conversion. When the reaction mixture is permitted to remain at reaction conditions for periods in excess of those defined, the amount of additional conversion obtained is small and there is a tendency for the desired glutaric acid to degrade to succinic acid. Accordingly, when the desired reaction time is reached, reaction is terminated and recovery of product is effected. These reaction times are in addition to induction periods.

The reaction mixture is preferably well agitated to insure good contacting of the reactants. Agitation can be provided by mechanical stirring devices aided by the ebullition caused by the introduction of the oxygen-containing gas below the surface of the liquid reaction mixture.

At the end of the reaction period the reaction mixture can be separated into its component parts by any convenient means. Thus, the contents of the reaction zone are cooled to room temperature, depressured and the reaction mixture withdrawn from the reaction zone. The reaction mixture is diluted with an equal volume of water and then heated on a steam bath to a temperature of about 100° C. for about ½ hour, or until the solution is pink, indicating the presence of cobaltous ions, and then evaporated to dryness. The residue is extracted with acetone to separate the organic products from the catalyst. The organic products will contain the desired glutaric acid and smaller amounts of succinic acid. The individual acids can be separated from each other in any conventional manner, for example, by crystallization from conventional solvents such as benzene or water. The catalyst will, at least in part, be present as the cobalt salt of glutaric and succinic acids. To recover these acids from the catalyst, the catalyst is treated with sodium hydroxide to release the chemically-bound acids from the catalyst, at the same time converting the cobalt salt to its hydroxide or oxide state. Filtration will result in a solution containing the acids as their sodium salts. The latter are sprung with hydrochloric acid to form the desired free acids. Recovery of these acids is effected by evaporating the solution to dryness and then extracting the residue with acetone to separate the acids from sodium chloride. Evaporation of acetone will leave behind the additional glutaric and succinic acids. The catalyst can also be treated with concentrated hydrochloric acid and on evaporation to dryness will result in the formation of free organic acids and inorganic salts. These can readily be separated by extraction with a solvent, such as acetone mentioned above. In a continuous oxidation procedure, the amount of product acids tied up with the cobalt will reach a steady-state concentration, and for practical reasons can be ignored in calculations.

DESCRIPTION OF PREFERRED EMBODIMENTS

Example I

A series of runs was carried out in which all of the components of a reaction mixture, except molecular oxygen, were added to a 1-liter, stirred, 316-stainless steel autoclave. The contents of the autoclave were heated to desired temperature and pressured with molecular oxygen to desired pressure. Time between the moment when the reaction mixture is brought to the defined temperature and pressure levels and when oxygen absorption begins (indicating the start of oxidation) is defined as the induction period. The time between the start of oxygen absorption and when the reaction mixture is withdrawn from the reaction conditions is defined as reaction time. The products obtained were then subjected to recovery procedures as defined above. The data obtained are set forth below in Table I. Conversion was calculated by dividing the weight of the cyclopentane reacted by the weight of the cyclopentane charged times one hundred. Efficiency was based on the percent of cyclopentane reacted that was converted to the indicated compound.

TABLE I

| Run No. | 1 | 2 | 3 |
|---|---|---|---|
| Charge | | | |
| Cobaltous Acetate Tetrahydrate, Grams | 5 | 5 | 1.5 |
| Millimols of Cobalt Metal Per Mole of Cyclopentane | 24 | 24 | 7.3 |
| Sodium Bromide, Grams | 2.5 | 0.3 | 0.5 |
| Acetic Acid, Grams | 400 | 400 | 400 |
| Cyclopentane, Grams | 58 | 58 | 58 |
| Reaction Conditions | | | |
| Temperature, ° C. | 100 | 100 | 100–115 |
| Partial Pressure of Oxygen, Pounds/Square Inch Gauge (Kilograms/Square Centimeter) | 300(20.4) | 300(20.4) | 300(20.4) |
| Induction Time, Minutes | 4 | 37 | Not detectable |
| Reaction Time, Hours | 2 | 1.8 | 5.6 |
| Product Data | | | |
| Conversion (Weight Per Cent Cyclopentane Reacted) | 90 | 88 | ~5 |
| Glutaric Acid, Grams (Selectivity) | 76.6(81.2) | 76.8(81.6) | [Total product = 4.3 grams] |
| Succinic Acid, Grams (Selectivity) | 15.8(18.8) | 15.4(18.4) | |

The data in Table I show that the amount of cobalt present in the reaction mixture is critical in order to obtain excellent conversions of cyclopentane and excellent selectivity to glutaric acid. In each of Runs Nos. 1 and 2 wherein the amount of cobalt was within the claimed critical range excellent conversions and selectivities were obtained. In Run No. 3, on the other hand, wherein only 7.3 millimols of cobalt were present per mol of cyclopentane the results were disastrous. The reaction mixture was heated at 100° C. for a period of 2.3 hours and no appreciable absorption of oxygen was noted. The reaction mixture was then raised to 115° C. and maintained at such level for an additional 3.3 hours. Again no appreciable absorption of oxygen was noted. The total reaction product, which was not analyzed, amounted to but 4.3 grams.

EXAMPLE II

An additional set of runs was carried out, as above. The results obtained are tabulated below in Table II.

TABLE II

| Run No. | 4 | 5 | 6 | 7 | 8 | 9 |
|---|---|---|---|---|---|---|
| Charge | | | | | | |
| Cobaltous Acetate | | | | | | |

TABLE II-continued

| Run No. | 4 | 5 | 6 | 7 | 8 | 9 |
|---|---|---|---|---|---|---|
| Tetrahydrate, Grams | 20 | 20 | 20 | 20 | 20 | 20 |
| Millimols of Cobalt Metal Per Mol of Cyclopentane | 96 | 96 | 96 | 96 | 96 | 48 |
| Methyl Ethyl Ketone, Grams | 10 | 10 | 10 | 10 | 10 | 15 |
| Acetic Acid, Grams | 400 | 400 | 400 | 400 | 400 | 400 |
| Cyclopentane, Grams | 70 | 70 | 70 | 70 | 70 | 58 |
| Reaction Conditions | | | | | | |
| Temperature, °C. | 80 | 90 | 100 | 115 | 125 | 110 |
| Partial Pressure of Oxygen, Pounds/Square Inch Gauge (Kilograms/Square Centimeter) | 300(20.4) | 300(20.4) | 300(20.4) | 300(20.4) | 300(20.4) | 150(10.2) |
| Induction Time, Minutes | 100* | 145 | 60 | 17 | 3 | 10 |
| Reaction Time, Hours | 3.0 | 2.4 | 2.6 | 1.5 | 0.7 | 2.8 |
| Product Data | | | | | | |
| Conversion (Weight Per Cent Cyclopentane Reacted) | 89 | 84 | 80 | 74 | 70 | 45 |
| Glutaric Acid, Grams (Selectivity)** | 99.8(85) | 91.2 (82) | 88.1(84) | 81.2(83) | 71.7(78) | 41.5(86) |
| Succinic Acid Grams (Selectivity)** | 15.5(15) | 18.1 (18) | 15.4(16) | 14.8(17) | 18.2(22) | 6.4(14) |

*In order to cut down on induction time, reaction mixture was heated at 110° C. for 100 minutes until oxygen absorption began and then the reaction mixture was reduced to reaction temperature of 100° C.
**Small amounts (from 1 to 2 weight per cent) of minor products formed during the reaction were ignored for calculation purposes.

Although in each of Runs Nos. 4, 5, 6, 7 and 8 excellent conversions of cyclopentane were obtained, surprisingly, best results were obtained at the lower temperatures. This is most desirable for commercial operation, since lower temperatures would reduce the cost of the operation and would lessen the possibilities of undue degradation of the product. In each of Runs Nos. 4, 5, 6, 7 and 8 excellent selectivities to glutaric acid were obtained. That the partial pressure of oxygen is critical can be seen from the data in Run No. 9. Even though sufficient cobalt was present, an oxygen partial pressure of 150 pounds per square inch resulted in a conversion of but 45 percent.

EXAMPLE III

Still another set of runs was carried out as above. The results obtained are tabulated below in Table III.

TABLE III

| Run No. | 10 | 11 | 12 | 13 | 14 |
|---|---|---|---|---|---|
| Charge | | | | | |
| Cobaltous Acetate Tetrahydrate, Grams | 20 | 10 | 5 | — | — |
| acetonate, Grams | — | — | — | 3.6 | 2.0 |
| Millimols of Cobalt Metal Per Mol of Cyclopentane | 99 | 49 | 25 | 12 | 8 |
| Methyl Ethyl Ketone, Grams | 10 | 10 | 10 | 5 | 5 |
| Acetic Acid, Grams | 400 | 400 | 400 | 400 | 400 |
| Cyclopentane, Grams | 58 | 58 | 58 | 58 | 58 |
| Reaction Conditions | | | | | |
| Temperature, °C. | 100 | 100 | 100 | 100 | 110 |
| Partial Pressure of Oxygen, Pounds/Square Inch Gauge (Kilograms/Square Centimeter) | 300(20.4) | 300(20.4) | 300(20.4) | 300(20.4) | 300(20.4) |
| Induction Time, Minutes | 69 | 38 | 145 | 65 | 65 |
| Reaction Time, Hours | 1.4 | 1.8 | 2.3 | 3.1 | 5.3 |
| Product Data | | | | | |
| Conversion (Weight Per Cent Cyclopentane Reacted) | 87 | 84 | 81 | 65 | <10 |
| Glutaric Acid, | | | | | |

TABLE III-continued

| Run No. | 10 | 11 | 12 | 13 | 14 |
|---|---|---|---|---|---|
| Grams (Selectivity)* | 75.6(81) | 74.5(80) | 70.4(80) | 58.1(81) | [Total Product= |
| Succinic Acid, Grams (Selectivity)* | 17.6(19) | 15.8(20) | 16.1(20) | 11.9(19) | 7.8 grams] |

*Small amounts (from 1 to 2 weight per cent) of minor products formed during the reaction were ignored for calculation purposes.

Note that in each of Runs Nos. 10, 11 and 12, wherein operation was conducted in strict compliance with the dictates herein excellent conversions of cyclopentane and excellent selectivities to glutaric acid were obtained. In Run No. 13 wherein the reaction conditions were in accordance with the requirements herein, but the amount of cobalt was not, appreciably lower conversion of cyclopentane was obtained. In Run No. 14 wherein the amount of cobalt was still further reduced only 7.8 grams of total product, not analyzed, was obtained.

EXAMPLE IV

That it is imperative that the temperature of reaction cannot be permitted to rise above the critical ranges defined above is apparent from the following. In order to optimize the production of glutaric acid herein, it became of interest to know whether or not glutaric acid is stable under the conditions defined herein. A reasonable approach would be simply to add glutaric acid to the cyclopentane oxidation charge and then determine the fate of the glutaric acid. This approach, however, would not differentiate between the glutaric acid added initially and the glutaric acid produced as a result of oxidation. Moreover, it might still be possible for glutaric acid to be stable under the reaction conditions and products, such as succinic acid, to form from cyclopentane by a different route.

To solve this problem we chose to study the oxidation of normal butane in the same system in the presence of glutaric acid. Accordingly, the runs reported above were repeated except that the charge contained normal butane in place of cyclopentane and also glutaric acid was present. The reactions were permitted to run until oxygen absorption ceased. The results are summarized below in Table IV.

TABLE IV

| Run No. | 15 | 16 | 17 |
|---|---|---|---|
| Charge | | | |
| Cobaltous Acetate Tetrahydrate, Grams | 20 | 20 | 20 |
| Methyl Ethyl Ketone, Grams | 15 | 15 | 15 |
| Normal Butane, Grams | 52 | 50 | 60 |
| Acetic Acid, Grams | 400 | 400 | 400 |
| Glutaric Acid, Grams | 40 | 40 | 40 |
| Reaction Conditions | | | |
| Temperature, °C. | 115 | 123 | 130 |
| Partial Pressure of Oxygen, Pounds/Square Inch Gauge (Kilograms/Square Centimeter) | 300(20.4) | 300(20.4) | 300(20.4) |
| Reaction Time, Hours | 1.2 | 2.0 | 2.0 |
| Product Data, Grams (Selectivity) | | | |
| Glutaric Acid | 40(100) | 34.4(86) | 31.6(79) |
| Succinic Acid | 0(0) | 5.0(14) | 8.4(21) |
| Recovery Data | | | |
| Glutaric Acid Degraded, | | | |

TABLE IV-continued

| Run No. | 15 | 16 | 17 |
|---|---|---|---|
| Weight Per Cent | 0 | 14 | 21 |
| Per Cent Glutaric Acid Degraded Per Hour | 0 | 7 | 10.5 |

The above data clearly show that it is critical to maintain the reaction at a temperature as low as possible and to terminate the reaction as soon as possible. In Run No. 15 at 115° C. no apparent degradation of glutaric acid was noted, and only a small amount in Run No. 16 at 123° C., whereas in Run No. 17 at 130° C. substantial degradation of glutaric acid to succinic acid occurred. However, as Run No. 8 in Table II shows, excellent selectivities to glutaric acid are still obtained at the higher temperature claimed herein.

Obviously, many modifications and variations of the invention, as hereinabove set forth, can be made without departing from the spirit and scope thereof, and therefore only such limitations should be imposed as are indicated in the appended claims.

We claim:

1. A process for converting cyclopentane to glutaric acid in a system consisting essentially of cyclopentane, an aliphatic monobasic acid solvent, cobaltic ions and molecular oxygen, which comprises subjecting cyclopentane to oxidation with oxygen in the presence of cobaltic ions in an aliphatic monobasic acid having only primary and secondary hydrogen atoms and having two to eight carbon atoms, wherein at least about 20 millimols of cobalt are present per mol of cyclopentane, while maintaining a temperature of about 70° to about 150° C. and an oxygen partial pressure of at least about 175 pounds per square inch absolute for a period of about 0.5 to about 3 hours.

2. The process of claim 1 wherein about 25 to about 100 millimols of cobalt are present per mol of cyclopentane.

3. The process of claim 1 wherein the temperature is in the range of about 80° to about 120° C.

4. The process of claim 1 wherein the oxygen partial pressure is in the range of about 200 to about 500 pounds per square inch absolute.

5. The process of claim 1 wherein the time of reaction is in the range of about one to about two hours.

6. The process of claim 1 wherein the monobasic acid has from two to four carbon atoms.

7. The process of claim 1 wherein the monobasic acid is acetic acid.

8. The process of claim 1 wherein the molar ratio of monobasic acid to cyclopentane is about 1.5:1 to about 10:1.

9. The process of claim 1 wherein the molar ratio of monobasic acid to cyclopentane is about 3:1 to about 9:1.

* * * * *

UNITED STATES PATENT OFFICE
CERTIFICATE OF CORRECTION

Patent No. 4,158,739  Dated June 19, 1979

Inventor(s) Johann G. D. Schulz and Anatoli Onopchenko

It is certified that error appears in the above-identified patent and that said Letters Patent are hereby corrected as shown below:

COLUMNS 5 and 6, Table III

"acetonate, Grams" should read --Cobaltic Acetyl-acetonate, Grams--.

Signed and Sealed this

Sixth Day of November 1979

[SEAL]

Attest:

RUTH C. MASON
Attesting Officer

LUTRELLE F. PARKER
Acting Commissioner of Patents and Trademarks